United States Patent [19]
Johnston et al.

[11] 4,136,113
[45] Jan. 23, 1979

[54] PROCESS FOR PREPARATION OF ORGANIC ACID HALIDE

[75] Inventors: James D. Johnston; Richmond M. Starrett; Robert N. Sanders, all of Baton Rouge, La.

[73] Assignee: Ethyl Corporation, Richmond, Va.

[21] Appl. No.: 865,219

[22] Filed: Dec. 28, 1977

[51] Int. Cl.² .............................................. C07C 51/58
[52] U.S. Cl. ............................ 260/544 Y; 260/543 R; 260/544 L; 260/544 D
[58] Field of Search ........... 260/544 D, 544 Y, 543 R, 260/544 L

[56] References Cited
U.S. PATENT DOCUMENTS

| 944,372 | 12/1909 | Mugdan | 260/544 Y |
| 1,805,162 | 12/1931 | Britton | 260/544 Y |

OTHER PUBLICATIONS

Chemical Abstr., vol. 52, col. 3712(e).
Montonna, J. Am. Chem. Soc., vol. 49, pp. 2114-2116 (1927).
Groggins, "Unit Processes in Organic Chemistry" (1952), p. 237.
Olah, "Friedd-Crafts and Related Reactions", vol. I, pp. 283-290, 295 (1963).

Primary Examiner—Gerald A. Schwartz
Attorney, Agent, or Firm—Donald L. Johnson; John F. Sieberth; James M. Pelton

[57] ABSTRACT

A process for the preparation of organic acid halide such as acetyl chloride by reacting an organic acid anhydride with a silicon halide, such as silicon tetrachloride, under conditions such that such the organic acid halide is produced along with silica which is easily separated and disposed of. Preferred conditions include use of a solvent, use of a catalyst and additional process reaction steps whereby by-products are converted to additional organic acid halide and easily disposable waste products.

21 Claims, No Drawings

PROCESS FOR PREPARATION OF ORGANIC ACID HALIDE

BACKGROUND OF THE INVENTION

This application relates to a process for the preparation of organic acid chloride, more particularly it relates to a process for preparation of an organic acid chloride selected from alkyl and aryl organic acid chlorides and, particularly, to the preparation of acetyl chloride, benzoyl chloride and toluoyl chloride.

Many organic synthesis employ acid chlorides in their reactions. For example, acetyl chloride is used on a large scale as a catalyst in the chlorination of acetic acid. Usually in such cases, it is made in situ from acetic anhydride and by-product hydrogen chloride from the chlorination reaction. Unfortunately, in such processes only one-half of the available acetyl groups are utilized for the acetyl chloride, the remainder going to acetic acid. Acetyl chloride is a powerful acylating agent when used with aluminum chloride catalyst and will acetylate many compounds which cannot be acetylated with acetic acid or acetic anhydride. Acetyl chloride is also employed in the preparation of acetanilide, acetophenone and other industrial acetyl derivatives including anhydrides of carboxylic acids.

Several methods are known for preparation of organic acids, particularly acetyl chloride. According to Kirk-Othmer, *Encyclopedia of Chemical Technology*, Second Edition, Vol. 1, pages 138–142, acetyl chloride has been prepared by the action of chlorinating agents on acetic acid, its salts, esters or anhydrides, as indicated above by conveniently treating acetic anhydride with hydrogen chloride in situ. Although the foregoing method is used industrially for in situ production, normal laboratory preparations involve slow addition of phosphorus trichloride to acetic acid with cooling. Commercially, acetyl chloride is prepared by treating sulfur dioxide and chlorine with sodium acetate, followed by distillation.

In an article by Montonna, JACS, Vol. 49, pages 2114–2216 (1927), there is described a method for preparation of acid chlorides in which silicon tetrachloride is reacted with acetic acid or other appropriate organic acid at 50°-60° C. in various solvents to produce the organic acid chloride. The advantage of this reaction is indicated to be the preparation of "phosphorus- and sulfur-free" acid chlorides by the action of silicon tetrachloride on a corresponding organic acid. Yields of from about 50% up to 85% for acetyl chloride are given in various solvents such as aromatic hydrocarbons and ethers, although subsequent literature indicates Montonna's data to be suspect.

Although the Montonna method produces "phosphorus- and sulfur-free" organic acid chlorides, it suffers from the disadvantages of incomplete utilization of raw materials, production of complex by-products and evolution of much HCl.

Also, Dandegaonker, CA Vol. 62, 2700 (1965), is reported as reacting silicon tetrachloride with carboxylic acids, anhydrides and acid salts to give tetracetyloxysilanes and HCl, acyl chlorides and sodium chloride, respectvely. Decomposition of the tetracetyloxysilanes at greater than 200° C. was reported to yield the anhydrides. Further, Udovenko et al, CA Vol. 52, 3712D (1958), is reported to have reacted silicon tetrachloride with excess acetic anhydride to yield a precipitate of 80% silicon tetraacetate and acetyl chloride. The same products formed with other proportions of reactants but the products failed to precipitate if the ratio is under 1:4 silicon tetrachloride to acetic anhydride.

Benzoyl chloride may be prepared in many ways according to Kirk-Othmer, *Encyclopedia of Chemical Technology*, 2nd Edition, Vol. 3, p. 430–431, Interscience Publishers, New York (1964). For example, the partial hydrolysis of benzotrichloride; the chlorination of benzaldehyde and the reaction of benzoic acid with phosphorus pentachloride, phosgene or benzotrichloride, all afford benzoyl chloride. Large scale manufacture of benzoyl chloride for use as a benzoylating agent by which the benzoyl radical is introduced into alcohols, phenols, amines and other compounds through the Friedel-Crafts reaction and the Schotten-Baumann reaction are known. These reactions produce benzoyl peroxide, benzophenone, benzyl benzoate and other derivatives which have end uses in the dye, resin, perfume, pharmaceutical and polymerization catalyst fields. Toluoyl chloride has similar uses and can be produced in a similar manner from corresponding raw materials. In addition, the reaction of toluic acid with sulfonyl chloride or phosphoryl chloride also produces toluoyl chloride.

In view of this, the art has a need for an inexpensive organic acid chloride which is nevertheless free of sulfur- and phosphorus-containing residues. Such compounds would enjoy wide acceptance in the pharmaceutical industry.

THE INVENTION

Although reactions with silicon tetrachloride and organic acid anhydrides and acid salts have been reported, as shown hereinabove, the present invention provides an improved reaction whereby higher yields of desired acid chlorides can be produced, and, in a further aspect of the invention, the by-product silicon acetates can be reacted to provide additional amounts of product acid chloride. Such reactions have the advantage of simple procedure, easy separation of product and residue, and an easily disposable residue. In addition, the complete utilization of all starting materials renders the reaction entirely feasible from a practical standpoint. For example, both chlorine and organic group values are used efficiently in the process of this invention. This is particularly true when an acyl anhydride is employed as a starting material.

According to the process of the present invention, there is described an improved process for the preparation of an organic acid halide by contacting an organic acid or its anhydride and silicon tetrahalide in the presence of a catalytic amount of a Lewis acid, such as a metal halide, to obtain the organic acid halide reaction product which is easily separated from by-products produced in the reaction and which produces by-products which are easily disposable.

In another aspect of the invention there is provided an improved method for the preparation of organic acid halides which is an improved process for the preparation of acetyl chloride, said process including the reaction of acetic anhydride and an excess over the stoichiometric amount required to react with said acetic anhydride of silicon tetrachloride whereby there is produced a reaction mass containing acetyl chloride and a mixtue of compounds of the general formula

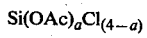

in which a is a whole number from 0 to 4, removing the acetyl chloride produced from the reaction mass and further reacting said reaction mass with excess silicon tetrachloride in the presence of a Lewis acid catalyst whereby an additional amount of acetyl halide is produced.

In another aspect of this invention there is provided an improved process for the preparation of organic acid halides by the reaction of an organic acid or its anhydride with a silicon halide which is selected from silicon tetrachloride and silicon tetrabromide, the improvement comprising conducting the process in the presence of a Lewis Acid catalyst and a solvent in which all reactants and catalyst are soluble at a temperature of from about 20° ot about 180° C. for a period of from about 0.5 to about 24 hours. Preferred catalysts employed in this preferred embodiment are aluminum chloride, stannic chloride and zinc chloride because these are soluble in preferred solvents such as halogenated hydrocarbons.

According to the present process, an organic acid or its anhydride is reacted with a silicon halide, preferably a silicon tetrahalide in which the halide is chlorine or bromine, under conditions such that an acid halide and a silicon compound are formed. In general, 2 moles of the organic acid or its anhydride are employed for each mole of silicon halide. The following equations are illustrative of the process using different starting materials:

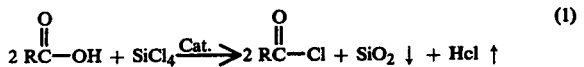

(1)

(2)

The organic group R in the above equations can be any aryl or alkyl group which forms an aromatic or aliphatic organic acid, which is not adversely affected by the reaction conditions, solvents and catalysts employed and which affords the production of the corresponding acid halide. Although the silicon tetrachloride was used illustratively, silicon tetrabromide can be used, of course, to prepare the desired organic acid bromide.

According to the process described hereinabove, the organic acid halide is typically prepared from aromatic and aliphatic organic acids and their anhydrides and mixed anhydrides in which each of the organic moieties are different. Preferably, in this invention the acids or anhydrides are typically those having acetic, propionic, butyric, isobutyric, toluic, phenylacetic, maleic, succinic, phthalic and benzoic groups. Although the foregoing acids and anhydrides are useful under somewhat different conditions, it is well within the scope of the skilled practioner to determine optimum conditions under which the particular acid or anhydride will best be converted to the acid chloride. Preferably, acetic, benzoic and toluic acids and anhydrides are most widely useful in chemical syntheses and best illustrate the process of the invention.

The acid or anhydride is reacted with a silicon tetrahalide, producing the corresponding acid halide and silica as a by-product, which is innocuous and easily disposable. Any of the silicon halides can be employed, although different compounds having different physical properties will require somewhat different temperatures within the scope of this invention for best results. Thus, the silicon halides employed are preferably silicon chloride and bromide, preferably, the tetrahalide and, most preferably, silicon tetrachloride, because of its availability, low cost and the preference in industry for using acid chlorides. Mixed silicon halides are known and can also be used; however, they suffer from the disadvantages of producing mixed acid halides which are usually not commercially desirable, or, if desired, nevertheless require separation of the acid halides into the individual components for use. Accordingly, it is preferable to have a single halide and more preferred to employ a tetrahalide, most preferably the tetrachloride, as a starting material.

For best results, the process of this invention employs a catalytic amount of a Lewis Acid catalyst, preferably a metal halide, such as ferric chloride, aluminum chloride, stannic chloride, zinc chloride or other transition metal halide. Ferric chloride is a useful catalytic metal halide in reactions conducted without a solvent. In other cases, reactions of the present invention may employ a metal halide Lewis Acid catalyst which is soluble in the reaction medium employed, for example, aluminum chloride, stannic chloride or zinc chloride. Good results are obtained when a soluble catalyst is used because of the ability of the soluble catalyst to mix intimately with the reactants. Only a sufficient amount of metal halide catalyst necessary to achieve increased yields over the non-catalytic process is required for the process of this invention. Thus, from a few crystals in a reaction flask to about 5 mole percent based on the amount of organic acid or anhydride employed can be used. Preferably from 1 to about 3 mole percent of metal halide Lewis Acid catalyst based on the organic acid or anhydride can be used in the process of this invention.

The reactions are run at temperatures which give good rates of reaction and practicable reaction times. Generally, the processes of the invention can be carried out at atmospheric or super atmospheric pressure and at or above the normal boiling point of the reaction medium. In many instances, an inert solvent, such as aromatic or aliphatic hydrocarbon or halides such as benzene, toluene, carbon tetrachloride, tetrachloroethane, nitrobenzene, and the like, can be used as a reaction medium. However, although the use of an inert solvent is not critical to the process of the invention and, in fact, it is possible in many cases to conduct the reaction without solvent to reduce processing costs, costs of recovery of product from the solvent, capital investment for equipment to separate product and solvent, etc; in general, the use of a solvent allows better contact of all reagents and catalyst and facilitates the reaction.

The reaction can be conducted by adding one reactant and the catalyst to the reactor, heating the mixture to reflux and adding a second reactant drop-wise or at a rate sufficient to provide good reaction. Alternatively, the reactants can be added together in the same reaction vessel, followed by heating to reflux and adding catalyst on reaching the desired temperature. As another alternative, the catalyst can be placed in the reaction vessel with solvent, heated to reflux and then both reactants can be simultaneously fed, drop-wise or at a rate sufficient to facilitate reaction. In one embodiment, all reactants, catalyst and solvent are in the reactor prior to heating the reaction mixture to the desired temperature. On completion of the reaction, the reaction mass may be filtered and product separated by distillation or recovered in any conventional manner. Generally, the organic acid chloride is removed from the reaction mass by distillation, vacuum flashing or similar vaporization from the reaction vessel or continuous distillation from the reaction mixture after separation from the reaction vessel.

The reaction mass remaining after removal of the product organic acid may contain silicon dioxide and unreacted starting material, as well as by-product silicon compounds generally having the formula

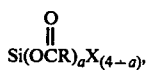

$$Si(OCR)_a X_{(4-a)},$$

in which R is an organic aromatic or aliphatic group as defined hereinbefore, X is the halide selected from chlorine and bromine and a is a whole number from 0 to 4. Of course, one preferred aspect of the process of this invention provides silicon chloroacetates of formula $Si(OAc)_a Cl_{(4-a)}$. When such silicon chloroacetates are produced, it has been found that they can be further reacted in the presence of additional amounts of silicon tetrachloride or Lewis Acid catalyst to produce additional amounts of organic acid halide and silica by-product. Such further reactions are generally carried out under the same conditions as the original reaction, although higher temperatures may be required to decrease reaction time.

The following examples illustrate the process of the present invention.

EXAMPLE 1

To a reaction vessel was added 17.1 grams of silicon tetrachloride and 20.4 grams of acetic anhydride. A few crystals of ferric chloride were added and the mixture slowly became warmer. The mixture was stirred under nitrogen and a reflux condenser and thermometer were attached to the reaction vessel. The mixture was heated to reflux at about 55° C. Thereafter, a distilling head was attached and the mixture was distilled at 48°-50° C. The distillate obtained was 96 + % pure and amounted to a yield of 84% acetyl chloride based on the starting acetic anhydride. A reddish-brown solid weighing 11.5 grams remained in the reaction vessel.

EXAMPLE 2

Example 1 was repeated with 17.1 g of silicon tetrachloride and 20.4 g of acetic anhydride mixed at room temperature. Then, a few crystals of ferric chloride were added and slight warming of the flask was noted. The contents were distilled at 50°-55° C. until no more distillate was obtained. A yield of acetyl chloride of 80% was obtained. The residue was reddish solid weighing about 12 g.

EXAMPLE 3

17.1 g of silicon tetrachloride and a few crystals, about 0.5 g, of ferric chloride were mixed under nitrogen and warmed to about 50° C. Then, there was added 20.4 g of acetic anhydride slowly with vigorous stirring. On completion of the acetic anhydride addition, the mixture was distilled to 50°-54° C. The distillate contained acetyl chloride by NMR with about 89% yield based on the starting silicon tetrachloride and the residue was a reddish-brown solid.

EXAMPLE 4

To the reaction vessel was added a few crystals, about 0.5 g, of ferric chloride under nitrogen. The flask was warmed to about 60° C. with an oil bath. Then, from two separatory addition funnels was added 17.1 g of silicon tetrachloride and 20.4 g of acetic anhydride at a molar ratio of about 1:2. On completing the addition of the silicon tetrachloride and acetic anhydride, a distilling head was attached to the reaction vessel and the reaction mass distilled at 50°-55° C. to give 17 g of distillate and 18 g of semi-solid residue. This amounts to about 29% conversion and about 75% yield of acetyl chloride based on silicon tetrachloride recovered.

EXAMPLE 5

To a reaction vessel was added 20.4 g of acetic anhydride and a few crystals of ferric chloride. These were mixed at room temperature and heated slowly with stirring to about 50°-60° C. At this point, 17.1 g of silicon tetrachloride was slowly, i.e., drop-wise, added with stirring. As soon as the silicon tetrachloride addition was completed, acetyl chloride began distilling at 50° C. and continued as the temperature rose slowly to greater than 90° C. The yield of acetyl chloride was 36.6%.

EXAMPLE 6 — Comparative

To a reaction vessel was added 17.1 g of silicon tetrachloride, 20.4 g of acetic anhydride, which was heated to reflux and stirred for 30 minutes. Analysis by NMR indicated the reaction mass contained 46% acetyl chloride and 54% silicon acetates. A distilled yield of about 41% acetyl chloride was obtained. After the acetyl chloride was distilled off, the distillation did not shift the equilibrium toward production of acetyl chloride or affect the semi-solid silicon acetate residue. The reactor was cooled and more silicon tetrachloride was added to the reaction mixture. On heating to 100° C., the reaction mass became a clear liquid which contained only silicon chloroacetates.

EXAMPLE 7

To a reaction vessel was added 17.1 g of silicon tetrachloride and 20.4 g of acetic anhydride. The reaction mixture was stirred for 30 minutes at room temperature. Then, the reactor contents were heated and 14.0 g of acetyl chloride distilled. The residue was cooled and treated by adding 0.5 g of ferric chloride catalyst. The reactor was again heated and an additional 11.4 g of acetyl chloride distilled off. There remained 11.0 g of residue which was in a reddish solid in the pot. This residue was cooled and there was added to it an additional 17.1 g of silicon tetrachloride and 24 g of acetic anhydride. The mixture was distilled and 22 g of acetyl chloride was obtained. The residue was cooled and 5 g of silicon tetrachloride amounting to 30% excess over the original stoichiometry, was added. The reaction mixture was distilled to obtain 6.5 g additional acetyl chloride. The total condensed overhead from the second run was 29.5 g which amounted to 94.5% of the theoretical based on the acetic anhydride added. The residue from this second run amounted to 28 g or a total of about 78 g of residue as opposed to a theoretical amount of about 80.5 g, total amount of theoretical solids.

Accordingly, it can be seen that when little catalyst and excess silicon tetrachloride are employed, greater than the expected 50% reaction of silicon tetrachloride and acetic anhydride are achieved. This is especially important in view of the fact that in early experiments the reaction of silicon tetrachloride and acetic anhydride in the presence of benzene solvent gave no reaction at all. Generally, in the presence of solvent and without the use of catalyst, the reaction gives a mixture of about equal parts of acetyl chloride and silicon chloroacetates. Distillation of the acetyl chloride produced in such a process amounts to about 45% conversion to acetyl chloride leaving a residue of the silicon chloroacetates.

The reaction of acetic anhydride with silicon tetrachloride was studied to determine the effect on the reaction of different solvents, temperatures, reaction times and catalysts. In general, the reaction was conducted by adding the acetic anhydride, solvent and catalyst to a 3-necked, creased flask equipped with dropping funnel, stirrer and reflux condenser. The reaction flask contents were heated to reflux and then the silicon tetrachloride was added at a rate such that the condenser was not flooded. Samples were taken by removing the dropping funnel and inserting a long needle hypodermic syringe and analyzed by NMR. The particular solvents, temperatures, amounts, times and results of each example are given in the table below:

TABLE I

Variable Study of the Reaction of Acetic Anhydride and Silicon Tetrachloride

| Ex. No. | Moles of Reactant | | Conditions | | | | % Yield of AcCl[b] |
|---|---|---|---|---|---|---|---|
| | $SiCl_4$ | $Ac_2O$[a] | Solvent (Amt.) | Temp. (°C) | Time (hr.) | Cat. | |
| 8 | 0.16 | 0.40 | heavy turbine oil[c] | 60 | 1 | $FeCl_3$(1 g) | 43.7 |
| 9 | 0.44 | 0.80 | " | 73 | 0.5 | $FeCl_3$(2 g) | 68.6 |
| 10 | 0.61 | 0.83 | " | 87 | 1.5 | $FeCl_3$(4 g) | 49.4 |
| 11 | 0.09 | 0.04 | $CCl_4$ (50 ml) | Ambient | 24 | $SnCl_4$(2.2 g) | 85 |
| 12 | 0.61 | 0.83 | $CCl_4$ (200 ml) | 60 | 5 | $SnCl_4$(5.5 g) | 62 |
| 13 | 0.30 | 0.41 | $CCl_4$ (200 ml) | 73 | 1 | $SnCl_4$(5.5 g) | 58 |
| 14 | 0.20 | 0.60 | $C_2H_2Cl_4$ (300 ml) | 90–120 | 12 | $SnCl_4$(5.5 g) | (d) |

[a]$Ac_2O$ — acetic anhydride
[b]AcCl — acetyl chloride, based on acetic anhydride
[c]A clear, pale yellow, high viscosity, low voltility hydrocarebon oil sold by Chevron Oil Co. and believed to be polyaromatic hydrocarbon; used as turbine oil, vacuum pump oil, etc.
[d]Entire system became very viscous From the above results, it can be seen that long reaction times with a rather concentrated solution and ambient temperatures are favored. Also, it appears that stannic chloride is a better catalyst than is ferric chloride under certain conditions.

The rate of reaction was studied under different reaction conditions using a procedure similar to Examples 8–14, except that a double reflux condenser was employed, internal magnetic stirring was used and samples were removed by hypodermic syringe through a rubber septum placed over the neck of the reaction flask previously having the stirrer. The conditions and results of those experiments are given in the following Table II:

From the foregoing results, it can be concluded that the reaction goes essentially to completion at ambient temperature with a catalyst, but is very slow. At a temperature of 50° C., the 25% yield level is achieved in about 1.5 hours. At 80° C. nearly 50% of the expected acetyl chloride is obtained in 6 hours with $SnCl_4$, but it appears in less than 2 hours with $AlCl_3$. However, when the temperature is increased to 140° C. using tetrachloroethane solvent and stannic chloride catalyst, almost 90% yield is reached in 5 hours. From observations of this system and examples using ferric chloride, the catalyst is more efficient when it is soluble in the reaction system, e.g., $SnCl_4$, $AlCl_3$, but not as effective when it is not soluble, e.g., $FeCl_3$.

Similar results are obtained when acetic anhydride is replaced with propionic, butyric and similar organic acid anhydrides.

The aromatic organic acids and anhydrides can also be reacted with silicon tetrahalides to produce the corresponding aromatic organic acid chlorides. For example, benzoic acid, benzoic anhydride, toluic acid and toluic acid and toluic anhydride all react under various conditions of solvent, temperature, catalyst, etc. to provide benzoyl and toluoyl halides, especially, benzoyl and toluoyl chloride. The following examples illustrate the reaction of benzoic acid and benzoic anhydride with silicon tetrachloride.

EXAMPLE 20 — Comparative

To a suitable reaction flask was added 20 grams (0.09 moles) of benzoic anhydride 7.6 grams (0.045 moles) of silicon tetrachloride and 150 ml of tetrachloroethane. Then, 21.6 g of tetradecane was added as an internal standard. The reaction mixture was heated to 130° and a sample was taken which contained 0.6% benzoyl chloride by the Vapor Phase Chromatograph internal

TABLE II

Rate of Appearance of Acetyl Chloride Over Time

| Ex. No. | Reactants (g.) | | Conditions, Temp. | Catalyst | Solvent | Results - time, Hours, of Yield of Acetyl Chloride | | | |
|---|---|---|---|---|---|---|---|---|---|
| | $SiCl_4$ | Acetic Anhydride | | | | 25% | 50% | 75% | Highest |
| 15 | 20.4 | 23.6 | Ambient | $SnCl_4$ | $CH_2Cl_2$ | 16 | 56 | 100 | 144 (85.5%) |
| 16 | 21.3 | 23.6 | 50° (1st 24 hrs.) Ambient balance | $SnCl_4$ | $CH_2Cl_2$ | 1.5 | 28 | 84 | |
| 17 | 20.7 | 25.3 | 80° | $SnCl_4$ | $CCl_4$ | >1 | 6 | 24 | 48 (96%) |
| 18 | 21.2 | 24.7 | 80° | $AlCl_3$ | $C_2H_2Cl_4$ | >1 | >2 | 4 | 8 (82.5%) |
| 19 | 21.8 | 25.3 | 80° (1st hr.) 140° (thereafter) | $SnCl_4$ | $C_2H_2Cl_4$ | >1 | >2 | 2 | 5 (89.5%) | standard method. A second sample taken two hours after the first when the temperature was 140° C. analyzed 68.5% benzoyl chloride. At this point all starting benzoic anhydride had disappeared. A third sample taken 4.5 hours after the first analyzed 73.6% benzoyl chloride, as did a fourth sample taken 6.5-7 hours after the first. The reaction mixture was kept at 140° C. overnight and a final sample taken after over 24 hours analyzed 85.7% benzoyl chloride by the VPC internal standard method.

The reaction mixture was fractionated and 29.4 grams of a fraction boiling at 95°-150° C. was obtained, analyzed by VPC, and calculated to be about 9.88 grams of benzoyl chloride for about a 38% yield of benzoyl chloride based on the starting benzoic anhydride.

EXAMPLE 21

The above comparative Example 20 was repeated except that 100 ml of tetrachloroethane was used and 0.25 grams of $AlCl_3$ (2 mole percent based on benzoic anhydride) was added. The mixture was stirred for one hour at room temperature to insure that the catalyst was dissolved and then the reactor contents were heated to 140° C. Samples taken after a period of 3 hours at a temperature of 130°-140° C. analyzed 91% benzoyl chloride. Indications of gell formation and very little stirring were apparent after 4 hours at temperature. The reactor contents were then cooled and distilled under vacuum. A fraction containing 157.6 grams was analyzed by NMR to be 15.4 mole % benzoyl chloride or equivalent to 21.5 grams of benzoyl chloride. Thus, there was obtained an 85% yield of benzoyl chloride based on the starting benzoic anhydride. This yield was confirmed by analysis of a sample by VPC.

EXAMPLE 22 — Comparative

To a reaction vessel was added a mixture of 15 grams (0.123 moles) of benzoic acid dissolved in 100 ml of tetrachloroethane. The mixture was stirred at room temperature while 10.4 grams (0.061 moles) of silicon tetrachloride were added dropwise. A sample was taken when addition of the silicon tetrachloride was completed and the reactor contents were heated to 140° C. After 20 hours at a temperature of 140° C. a sample was analyzed by VPC to contain 35 weight percent of benzoyl chloride. Upon cooling and then distilling 135.8 grams of overhead condensate were obtained. Analysis by NMR and VPC agreed fairly closely, indicating a 22.8% yield of benzoyl chloride based on starting benzoic acid. It was also noted during the run that HCl gas evolved.

EXAMPLE 23

Example 22 was repeated with the exception that 0.33 grams (2 mole percent based on benzoic acid) of $AlCl_3$ were added to the reaction vessel. After over 20 hours at a temperature of 140° C., a sample analyzed by VPC showed 46.7 weight percent benzoyl chloride.

EXAMPLE 24 — Comparative

A. Toluic Acid

To a reaction vessel was added 5 grams (0.037 moles) of para toluic acid suspended in about 100 ml of benzene. Then, 3.14 grams (0.0185 moles) of silicon tetrachloride were added and the reaction mixture stirred at room temperature. A small amount of HCl gas evolved during this stirring. Even though a small amount of material remained undissolved, the reaction mixture was distilled at 80° C. and atmospheric pressure. The overhead condensate contained only benzene and silicon tetrachloride. The pot residue was further heated until p-toluic acid sublimed. Analysis of the liquid remaining in the pot showed it to contain what is probably a silicon chloro toluate.

B. Toluic Anhydride

To a reaction vessel was added 5 grams (0.02 moles) of p-toluic anhydride dissolved in 150 ml of ethyl ether. The reaction vessel contents were heated to reflux which was maintained while 3.4 grams (0.02 moles) of silicon tetrachloride were added. The reactor contents refluxed for 30 minutes after addition of the silicon tetrachloride. Then the ether was distilled off leaving a white solid. This was further distilled under vacuum which left the white solid in the overhead condenser. No toluoyl chloride was obtained.

In contrast to the foregoing Example 24, toluic acid and mixtures of toluic acid and toluic anhydride were reacted with silicon tetrachloride in accord with the present invention. According to the procedure used, a known amount of the toluic acid or toluic acid/anhydride mixture is dissolved in tetrachloroethane and then silicon tetrachloride and catalyst are added. The reaction mixture is heated to reflux at 140°-150° C. for 5 to about 24 hours. The reaction contents are then distilled and analyzed to determine the yield of toluoyl chloride. The results and conditions of several examples following this procedure are given in Table III:

TABLE III

| | Toluic Acid/Ahydride Reaction With $SiCl_4$ | | | | | | | | |
|---|---|---|---|---|---|---|---|---|---|
| | Reactants (grams) | | | Conditions | | | | Toluoyl Chloride | |
| Example No. | Toluic Acid | Toluic Anhydride | $SiCl_4$ | Cat. Amt. (g) | Solvent Amount (ml) | Temp. °C | Time (hr.) | Wt. %, After Hrs. at Temp. | % Yield Distilled |
| 25 | 15 | 0 | 9.35 | $AlCl_3$ 0.3 | Tetrachloroethane 125 | 140 | 4.5 | 56 – 1.5 | — |
| 26 | 8.8 | 3.81 | 5.53 | — | " 50 | 140 | 20 | 73 – 20 | 75 |
| 27 | 1.65 | 3.85 | 2.43 | $AlCl_3$ 0.06 | " 50 | 140 | 5 | 95 – 5 | — |

From the above results, it is clear that the use of catalytic amounts of Lewis Acid metal halides greatly facilitate the reaction. Replacement of silicon tetrachloride in any of the above examples of this invention with silicon tetrabromide affords the corresponding acid bromide. Further, phenyl acetic acid could be used in place of toluic or benzoic acid.

In accord with the process described for the invention above, it can be seen that numerous variations and modification of the process can be made without departing from the scope of the invention. Therefore, it is desired that the protection afforded to the invention is limited only within the lawful scope of the following claims.

What is claimed is:

1. A process for the preparation of an organic acid chloride by contacting an organic acid or acid anhydride selected from aromatic carboxylic acids and anhydrides having from 6 to about 10 carbon atoms and aliphatic carboxylic acids and anhydrides having from 2 to about 6 carbon atoms and silicon tetrachloride in the presence of a catalytic amount of metal halide to obtain the corresponding organic acid chloride.

2. The process of claim 1 wherein said organic acid or acid anhydride is an organic acid anhydride which is a carboxylic acid anhydride having from 2 to about 6 carbon atoms in the molecule.

3. The process of claim 1 wherein said organic acid or acid anhydride is an organic acid anhydride which is a saturated lower aliphatic carboxylic acid anhydride.

4. The process of claim 1 wherein said organic acid or acid anhydride is an organic acid which is selected from acetic acid and propionic acid.

5. The process of claim 1 wherein said organic acid or acid anhydride is an organic acid anhydride which is acetic anhydride.

6. The process of claim 1 wherein said organic acid or acid anhydride is an organic acid selected from toluic acid and benzoic acid.

7. The process of claim 1 wherein said organic acid or acid anhydride is an organic acid which is toluic acid.

8. The process of claim 1 wherein said organic acid or acid anhydride is an organic acid which is benzoic acid.

9. The process of claim 1 wherein said silicon tetrachloride compound is employed in a stoichiometric amount.

10. The process of claim 1 wherein said metal halide catalyst is a ferric chloride.

11. The process of claim 1 wherein said metal halide catalyst is selected from aluminum chloride, stannic chloride and zinc chloride.

12. The process of claim 1 wherein said organic acid anhydride is acetic anhydride, said metal halide is aluminum chloride, said silicon tetrachloride is in a stoichiometric amount and a by-product silica is produced and precipitates as a granular solid from the reaction mixture on formation.

13. The process of claim 1 wherein said process is carried out in a reaction medium selected from chlorinated aliphatic hydrocarbon compounds having from 1 to about 4 carbon atoms, and mononuclear aromatic hydrocarbon compounds having from 6 to about 8 carbon atoms.

14. The process of claim 13 in which said process is carried out in a reaction medium selected from methylene chloride, chloroform, carbon tetrachloride, tetrachloroethane and hexachlorobutadiene.

15. The process of claim 13 in which said reaction medium is carbon tetrachloride.

16. The process of claim 13 in which said reaction medium is tetrachloroethane.

17. The process of claim 13 in which said metal halide catalyst is soluble in said reaction medium.

18. The process of claim 13 wherein said Lewis Acid catalyst is stannic chloride.

19. The process of claim 13 wherein said Lewis Acid catalyst is aluminum chloride.

20. The process of claim 21 wherein said acetyl chloride is removed from the reaction mass by distillation prior to said further reacting.

21. A process for the preparation of acetyl chloride, said process including the reaction of acetic anhydride and an excess over the stoichiometric amount required to react with said acetic anhydride of silicon tetrachloride whereby there is produced a reaction mass containing acetyl chloride and a mixture of compounds having the general formula $$Si(OAc)_a Cl_{(4-a)}$$

in which a is a whole number from 0 to 4, removing the acetyl chloride produced from the reaction mass and further reacting said reaction mass with the excess silicon tetrachloride in the presence of a Lewis Acid metal halide catalyst whereby an additional amount of acetyl chloride is produced.

* * * * *

UNITED STATES PATENT OFFICE
CERTIFICATE OF CORRECTION

PATENT NO. : 4,136,113

DATED : January 23, 1979

INVENTOR(S) : James D. Johnston et al

It is certified that error appears in the above-identified patent and that said Letters Patent are hereby corrected as shown below:

Column 2, Line 65, "mixtue" should read -- mixture --.
Column 7, Table I, Example 11, under "solvent" column,
"(50$^4$ml)" should read -- (50 ml) --. Column 7, Table I,
Footnote (c), "hydrocarebor" should read -- hydrocarbon --.
Columns 9 and 10, Table III, Example 27, under "Cat. Amt."
column, add -- 0.06 --. Columns 9 and 10, Table III, Example
27, under "Solvent Amount" column, delete "0.06" and
substitute therefor -- 50 --. Columns 9 and 10, Table III,
Example 27, under "Temp." column, delete "50".

Signed and Sealed this

Fifth Day of June 1979

[SEAL]

Attest:

RUTH C. MASON
Attesting Officer

DONALD W. BANNER
Commissioner of Patents and Trademarks